United States Patent [19]

Bauman et al.

[11] Patent Number: 5,180,824
[45] Date of Patent: Jan. 19, 1993

[54] 6-AZIDO-2-FLUOROPURINE, USEFUL IN THE SYNTHESIS OF NUCLEOSIDES

[75] Inventors: John G. Bauman, Alameda; Randolph C. Wirsching, Livermore, both of Calif.

[73] Assignee: Berlex Biosciences Inc., Alameda, Calif.

[21] Appl. No.: 620,236

[22] Filed: Nov. 29, 1990

[51] Int. Cl.$^5$ .................... C07D 473/40; C07H 19/20
[52] U.S. Cl. .................................. 544/251; 544/277; 536/27.4; 536/26.71
[58] Field of Search ............................... 544/277, 251

[56] References Cited

U.S. PATENT DOCUMENTS

| | | | |
|---|---|---|---|
| 4,188,378 | 2/1980 | Montgomery | 424/180 |
| 4,199,574 | 4/1980 | Schaeffer | 424/200 |
| 4,210,745 | 7/1980 | Montgomery | 536/26 |
| 4,357,324 | 11/1982 | Montgomery et al. | 424/180 |
| 4,609,661 | 9/1986 | Verheyden et al. | 514/262 |
| 4,963,662 | 10/1990 | Matthes et al. | 536/23 |
| 4,968,674 | 11/1990 | Taniyama et al. | 514/63 |

FOREIGN PATENT DOCUMENTS

| | | |
|---|---|---|
| 0254268 | 7/1987 | European Pat. Off. . |
| 0047399 | 11/1972 | Japan .................................. 544/277 |

OTHER PUBLICATIONS

Temple et al., "Studies on the Azidoazomethine-Tetrazole Equilibrium, V. 2- and 6-Azidopurines," J. Org. Chem., 1966, 31, 2210-15.
Montgomery et al., "Nucleosides of 2-Fluoroadenine," J. Med. Chem., 1969, 12, 498-504.
Montgomery et a., "The Synthesis of a Metabolically Stable Derivative . . . ," Townsend (ed.), Nucleic Acid Chemistry, pp. 156-160, 1986.
Montgomery et al., "Synthesis of Potential Anticancer Agents, XX, 2-Fluoropurines," JACS, 1960, 82, 463-68.
Eaton et al., "Convenient Synthesis of 2-Fluoroadenine," J. Org. Chem., 1969, 34, 747-48.
Montgomery, "The Chemistry and Biology of Nucleosides of Purines and Ring Analogs," Rideout (ed.), Nucleosides, Nucleotides, and Their Biological Applications, Proc. 5th Intl. Round Table, pp. 19-16, Oct. 20-22, 1982.
Olah et al., "Synthetic Methods and Reactions, 63, Pyridinium . . . ," J. Org. Chem., vol. 44, No. 22, 1979, pp. 3872-3881.
Huang et al., "Analogs of 2'-Deoxyadenosine: Facile Enzymatic Preparation and Growth Inhibitory . . . ," Biochem. Pharm., vol. 30, No. 19, 2663-71, '81.
Carson et al., "Synthesis of 2',3'-Dideoxynucleosides by Enzymatic Transglycosylation," Biochemical and Biophysical Research Communications, vol. 155, No. 2, 1988, pp. 829-834.
LaMontagne et al., "Preparation of 7-Substituted Pyrrolo(2,3-d)pyrimidines and 9-Substituted Purines as Potential Antiparasitic Agents," J. Heterocyclic Chem., 20, 295 (1983).
Glaudemans et al., "Syntheses with Partially Benzylated Sugars, 111, A Simple Pathway to a 'cis-Nucleoside'. . . ," J. Org. Chem. vol. 28, Nov. 1963, pp. 3004-3006.

*Primary Examiner*—Diana Rivers
*Attorney, Agent, or Firm*—Millen, White, Zelano and Branigan

[57] ABSTRACT

This invention pertains to novel methods of synthesizing fludarabine, fludarabine phosphate and related nucleoside pharmacologic agents utilizing 6-azido-2-fluoropurine as a novel intermediate.

In particular this invention pertains to a synthesis of fludarabine where the relatively low yield fluorination step is done before the costly coupling step.

16 Claims, No Drawings

6-AZIDO-2-FLUOROPURINE, USEFUL IN THE SYNTHESIS OF NUCLEOSIDES

BACKGROUND OF THE INVENTION

This invention relates to a composition of matter and a method for producing the same, and is particularly related to the compound 6-azido-2-fluoropurine, useful in the synthesis of fludarabine or fludarabine phosphate and related nucleoside pharmacologic agents.

Fludarabine phosphate, also known as 9-β-D-arabinofuranosyl-2-fluoroadenine-5'-phosphate, is a prodrug of the anti-cancer agent, 9-β-D-arabinofuranosyl-2-fluoroadenine. Accordingly, fludarabine phosphate is a chemotherapeutically effective form of the drug and is converted to the parent drug in vivo. U.S. Pat. No. 4,210,745 discloses one method of synthesizing the anti-cancer agent and U.S. Pat. No. 4,357,324 teaches the phosphorylation of said agent to yield fludarabine phosphate. In summary, fludarabine and fludarabine phosphate are commonly made by the following process:

(a) acetylation: 2,6-diaminopurine (also referred to as 2-aminoadenine) in a mixture of pyridine and acetic anhydride is refluxed to yield 2,6-diacetamidopurine, thus protecting the amino groups with acetyl groups;

(b) coupling: 2,3,5-tri-O-benzyl-1-O-p-nitrobenzoyl-D-arabinofuranose is converted to its corresponding chlorosugar 2,3,5-tri-O-benzyl-1-chloro-α-D-arabinofuranose, which is then coupled with 2,6-diacetamidopurine in ethylene dichloride in the presence of molecular sieves for several days until all of the chlorosugar is consumed, to yield the protected nucleoside 2,6-diacetamido-9-(2,3,5-tri-O-benzyl-β-D-arabinofuranosyl)purine;

(c) deacetylation: the protected nucleoside is refluxed with methanolic sodium methoxide to remove the acetyl groups yielding the nucleoside 2-amino-9-(2,3,5-tri-O-benzyl-β-D-arabinofuranosyl)adenine;

(d) diazotization/fluorination: the protected nucleoside of step (c) undergoes diazotization and fluorination by reaction with sodium nitrite and fluoboric acid in a tetrahydrofuranfluoboric acid (THF-HBF$_4$) system, to yield 9-(2,3,5-tri-O-benzyl-β-D-arabinofuranosyl)-2-fluoroadenine;

(e) debenzylation: the product from step (d) is treated with boron trichloride to remove the benzyl protecting groups; and lastly (f) phosphorylation: the product from step (e) is mixed with phosphorous oxychloride in an alkyl phosphate followed by hydrolysis in water, to yield 9-β-D-arabinofuranosyl-2-fluoroadenine-5'-phosphate, or fludarabine phosphate.

One of the disadvantages of this process is that the chlorosugar used in step (b) is very costly. Since the diazotization/fluorination reaction in step (d) has a relatively low yield, much of the chlorosugar is similarly wasted. Therefore, one way to improve this process is by introducing the 2-fluoro group before the coupling step. In this manner, the amount of chlorosugar needed for a given yield, will be reduced. This invention provides one such means of improving the fludarabine synthesis, along with providing a more convergent synthesis of other nucleosides.

SUMMARY OF THE INVENTION

This invention pertains to novel methods of synthesizing fludarabine, fludarabine phosphate and related nucleoside pharmacologic agents utilizing 6-azido-2-fluoropurine as a novel intermediate.

In particular this invention pertains to a synthesis of fludarabine where the relatively low yield fluorination step is done before the costly coupling step.

DETAILED DESCRIPTION OF THE INVENTION

The novel compound of this invention is 6-azido-2-fluoropurine (3), which is synthesized by the following scheme. First, 2-amino-6-chloropurine (1) is heated with an alkali metal azide and a polar solvent to yield 2-amino-6-azidopurine (2):

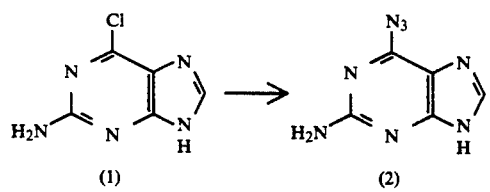

Suitable alkali metal azides include lithium azide (LiN$_3$), sodium azide (NaN$_3$) and potassium azide (KN$_3$), with the preferred alkali metal azide being NaN$_3$. The preferred solvent is aqueous dimethyl sulfoxide (DMSO). Reaction temperatures of 50°-130° C. are acceptable, however, 100°-110° C. is the preferred range. The reaction time may vary from 1 to 48 hours, however, the preferred time is 12 to 24 hours.

Second, compound (2) undergoes diazotization and fluorination reactions to yield the novel compound, 6-azido-2-fluoropurine (3):

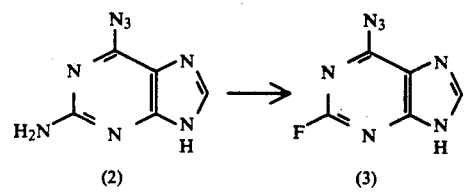

Suitable media for carrying out the diazotization and fluorination reactions of this invention comprise a diazotization agent, one or more fluorination agents and one or more polar solvents.

Suitable diazotization agents are nitrites, which include, without limitation, alkyl nitrites such as isobutyl nitrite and in particular tertiary alkyl nitrites such as t-butylnitrile, and alkali metal nitrites such as sodium and potassium nitrite.

Suitable fluorination agents include, without limitation, hydrogen fluoride (HF) and fluoboric acid (HBF$_4$) or salts thereof. The solvents can be anhydrous or aqueous and include, without limitation, water, pyridine and tetrahydrofuran (THF).

The preferred medium is an alkyl nitrite, aqueous fluoboric acid and THF.

The reaction temperature may be varied over a wide range between $-30°$ C. and 60° C. Preferably the reaction is begun below 0° C. and allowed to warm to ambient temperature over the course of 10 minutes to 3 hours and may be heated briefly to complete the reaction.

Azidopurine compounds such as (2) and (3) and their nucleoside derivatives can be represented by the general structure (A) wherein X is fluoro or amino and R is hydrogen or (protected)sugar. These compounds may exist in equilibrium with the corresponding tetrazolo-tautomer (B).

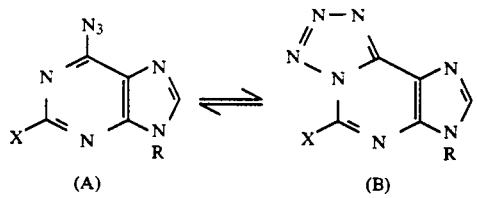

The ratio of tautomers (A) and (B) may depend on a number of factors such as the state of the sample (i.e. solid vs. solution), the nature of the solvent when the sample is in solution, the pH of the solution and on the identity of X. Evidence of this equilibration of structures (A) and (B) may be seen by the spectroscopic techniques used for characterization of these compounds, however it does not detract from the utility of these compounds as synthetic intermediates. For purposes of clarity these compounds will be represented and identified as 6-azidopurine tautomer (A). This representation is intended to include any and all ratios of the tautomeric formulas (A) and (B) wherein X and R are as defined herein.

The novel compound of this invention, 6-azido-2-fluoropurine, finds particular usefulness in the synthesis of nucleosides such as fludarabine and its prodrug, fludarabine phosphate. This synthesis begins with coupling 6-azido-2-fluoropurine (3) with a protected chlorosugar 2,3,5-tri-O-benzyl-1-chloro-α-D-arabinofuranose (4) to yield 6-azido-2-fluoro-9-(2,3,5-tri-O-benzyl-β-D-arabinofuranosyl)purine (5), (Bn=benzyl group). The chlorosugar (4) is readily synthesized by the reaction described in Glaudemans et al., J. Org. Chem. 28:3004–3006 (1963).

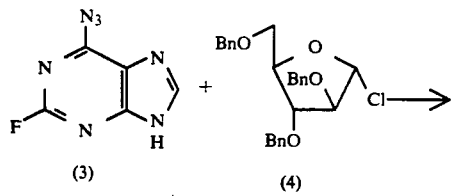

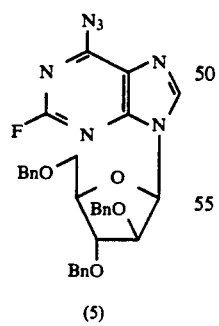

which is incorporated herein by reference, and the best results are obtained with freshly prepared chlorosugar.

The coupling of (3) with (4) may be accomplished in a variety of solvents with the aid of suitable catalysts or reagents. For example, the reaction may be performed in a halocarbon solvent such as ethylene dichloride or dichloromethane or in polar aprotic solvents such as acetonitrile, or N,N-dimethylformamide (DMF) or in mixtures thereof, in the presence of a tertiary amine reagent such as N,N-diisopropylethylamine. Molecular sieve may serve as a catalyst in these solvents in place of the tertiary amine. A hydride base such as sodium hydride may also be employed as a reagent; with a hydride base, however, polar aprotic solvents, or mixtures thereof, are preferred over halocarbon solvents. Reaction temperatures of 0° C. to 110° C. may be employed. However, temperatures between 20° C. and the reflux temperature of the solvent are preferred. Reaction times may vary from approximately 10 minutes to 7 days depending on the reaction temperature and on the catalyst or reagent used.

Catalytic hydrogenolysis of the protected nucleoside (5) reduces the azide to an amine and cleaves the O-benzyl groups to yield the nucleoside 9-β-D-arabinofuranosyl-2-fluoroadenine (6).

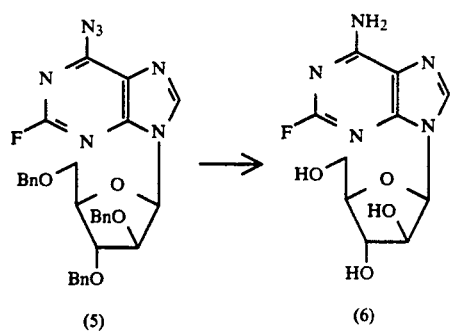

Preferably, this reaction is accomplished by conventional hydrogenation over a palladium catalyst in an alcoholic solvent. The results are generally improved by the addition of an acid catalyst such as aqueous hydrochloric acid to the reaction mixture. The required reaction time may vary from 1 hour to several days. Hydrogen pressures of 1 to 10 atmospheres (atm) are suitable, but the preferred pressure range is 2 to 5 atm.

Alternatively, in a more preferred process the reduction of the azide to an amine and the removal of the benzyl protecting groups can be accomplished in separate steps. First, 6-azido-2-fluoro-9-(2,3,5-tri-O-benzyl-β-D-arabinofuranosyl)purine (5) is converted to 9-(2,3,5-tri-O-benzyl-β-D-arabinofuranosyl)-2-fluoroadenine (7) by reaction with a suitable reducing agent.

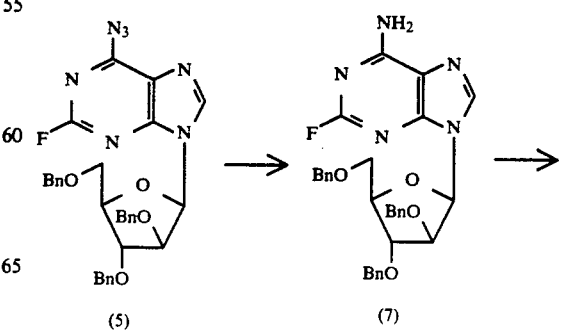

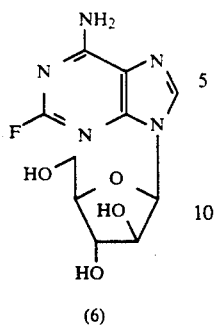

(6)

Without limitation, examples of suitable reducing reagents would include sodium borohydride or the combination of a dithiol and an amine such as 1,3-propanedithiol and triethylamine as described by Bayley et al Tetrahedron Lett. 3633-3364 (1978), which is incorporated herein by reference. With these reagents the reaction is best performed in an alcoholic solvent such as methanol, ethanol or 2-propanol or a mixture of alcoholic solvents, but water or nonprotic solvents may be added if desired. This reaction proceeds at temperatures of 0°-100° C., however in the preferred process, the reaction is begun at ambient temperature and may be heated to 50° (or to the normal boiling point of the solvent being used. Next, (7) is converted to 9-β-D-arabinofuranosyl-2-fluoroadenine (6). The process for this conversion has been set forth in U.S. Pat. No. 4,210,745 which is incorporated herein by reference. The two-step process has the advantage that the sensitive intermediate (5) need not be isolated.

If desired, 9-β-D-arabinofuranosyl-2-fluoroadenine (6) can be phosphorylated to yield 9-β-D-arabinofuranosyl-2-fluoroadenine-5'-phosphate (8). This phosphorylation involves the reaction of 9-β-D-arabinofuranosyl-2-fluoroadenine with

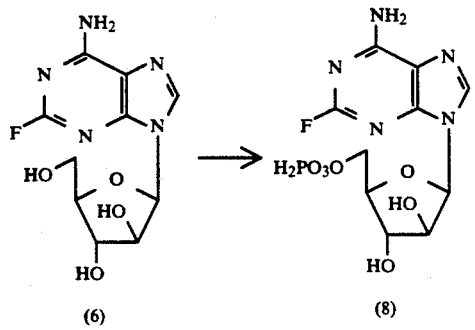

(6)    (8)

phosphorous oxychloride in an alkyl phosphate, followed by hydrolysis in water, and can be done according to the method set forth in U.S. Pat. No. 4,357,324, which is incorporated herein by reference.

In another embodiment, the novel compound of this invention (3) finds usefulness in the synthesis of 2-fluoroadenine (9):

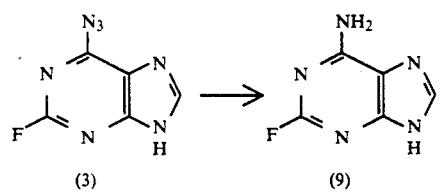

(3)    (9)

Reduction of the azide (3) to form 2-fluoroadenine (9) can be accomplished in several ways depending upon the intended use of the product. If the main goal is to obtain a high yield of 2-fluoroadenine and sulfur containing impurities can be tolerated, the reaction can be done with a dithiol-amine mixture such as 1,3-propanedithiol and triethylamine. This reaction may be carried in an alcoholic solvent and nonprotic modifiers may be added, however methanol is the preferred solvent because the product readily precipitates from the otherwise homogeneous mixture and is easily isolated by filtration. Temperatures of 0° to 100° C. may be used, however, ambient temperature is preferred. The reaction is complete within minutes at this temperature, however the best results are obtained when the mixture is allowed to stand for between 10 minutes and 4 hours to allow for complete precipitation of the product from solution. Alternatively, if sulfur containing impurities can not be tolerated, the reaction can be done with a hydride reducing agent such as sodium borohydride, as described hereinabove for the preparation of (7) from (5).

By either method, the product is easily isolated by filtration. These processes for the preparation of (9) have several advantages over methods previously described. Most importantly, the product is easily isolated in high purity by a simple filtration. The overall synthesis of 2-fluoroadenine (9) from 2-amino-6-chloropurine proceeds in good yield and no chromatographic separations are required, thus the process is easily amenable to scale-up.

Reaction of (9) with chlorosugar (4) under conditions as described herein above for the coupling of (3) and (4) provides an alternative process for the preparation of (7). This process is most preferred because the intermediate (7) is a solid and may be isolated by filtration after the coupling reaction.

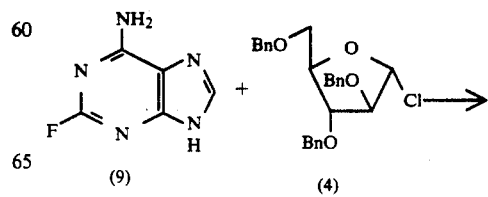

(9)    (4)

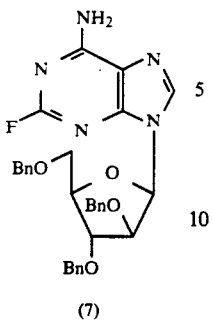

(7)

2-Fluoroadenine finds additional utility in that it can be enzymatically converted to (6) as reported by Montgomery in *Nucleosides, Nucleotides and their Biological Applications*, Rideout et al. eds, pp 19–46 (1985) via the procedure of Krenitsky et al., *Carbohydrate Research*, 47:139–146(1981).

EXAMPLE 1

Synthesis of 2-Amino-6-azidopurine

A solution of sodium azide (14.08 g, 0.216 mol) in water (35 mL) was added to a solution of 2-amino-6-chloropurine (28.27 g, 0.166 mol) in dimethyl sulfoxide (DMSO, 280 mL). The mixture was heated at 100°–110° C. for 24 h, then the resulting suspension was cooled and poured into 1.3 L of water. The precipitate was collected by filtration, washed with water and dried to afford 26.11 g of 2-amino-6-azidopurine, mp>260° C.; IR (KBr) 3313, 3146, 1678, 1641, 1551 cm$^{-1}$; $^1$H NMR (DMSO-d$_6$, 360 MHz) δ8.18 (s, 1H), 8.25 (bs, 2H), 13 (vbs, 1H); $^{13}$C NMR (DMSO-d$_6$, 90 MHz), 110.8, 138.7, 143.4, 145.7 , 146.1 ppm.

EXAMPLE 2

Synthesis of 6-Azido-2-fluoropurine

A solution of 2-amino-6-azidopurine (13.0 gm, 73.6 mmol) in tetrahydrofuran (THF, 163 mL), and 48% aqueous HBF$_4$ (42.24 mL) was cooled in a bath at −20° C. A solution of t-butylnitrite (12.65 mL) in THF (10 mL) was added over a 5 minute period. The bath was replaced with an ice-water bath for 30 minutes and then with a bath at 50° C. for 15 minutes. The mixture was then poured over ice (600 g), and water (200 mL) was added. The suspension was neutralized (pH 6-7) with saturated potassium carbonate (K$_2$CO$_3$), and ethyl acetate was added. The resulting solid potassium fluoborate (KBF$_4$) was collected by filtration and washed thoroughly with ethyl acetate. The aqueous layer was washed repeatedly with ethyl acetate and the combined ethyl acetate extracts were washed sequentially with water (500 mL) and saturated sodium chloride (NaCl) (250 mL) and dried over magnesium sulfate (MgSO$_4$) along with decolorizing carbon. The ethyl acetate was then filtered through celite and concentrated in vacuo to afford 9.36 g of the title compound. mp 190°–195° C. (d) (from ethyl acetate/pet. ether; The decomposition or melting point of this material varies from sample to sample); IR (KBr) 2240, 2200, 1620, 1595, 1565 cm$^{-1}$; MS (EI+, m/z) 179(M+, 55%), 151 ((M-N$_2$)+, 100%); 1H NMR (DMSO-d$_6$, 360 MHz) δ8.53 (s, 1H), 13.8 (bs, 1H); $^{13}$C NMR (DMSO-d$_6$, 90 MHz) 120 (very broad), 145.4 (broad), 152.2 (broad), 156 (very broad), 157.0 (d, J$_{CF}$=210 Hz) ppm; UV (MeOH) λ$_{max}$, 250, 286 nm.

EXAMPLE 3

Synthesis of 6-Azido-2-fluoro-9-(2,3,5-tri-O-benzyl-β-D-arabinofuranosyl)purine A solution of 2,3,5-tri-O-benzyl-1-α-D-arabinofuranosylchloride (freshly prepared from 1.9 g of 2,3,5-tri-O-benzyl-1-O-p-nitrobenzoyl-D-arabinofuranose), N,N-diisopropylethylamine (0.58 mL) and 6-azido-2-fluoropurine (0.50 g) in 10 mL of anhydrous 1,2-dichloroethane was heated at reflux overnight. Additional N,N-diisopropylethylamine (0.26 mL) was added and heating was continued for an additional 24 hours. The mixture was cooled to ambient temperature and diluted with dichloromethane (60 mL) and washed sequentially with 10% aqueous sodium hydroxide (NaOH), water, 1N phosphoric acid (H$_3$PO$_4$), saturated NaCl and then dried over MgSO$_4$ along with decolorizing carbon. The dried solution was filtered through celite and concentrated in vacuo. The residue was purified by silica gel chromatography with gradient elution from 3:1 Hexane:ethyl acetate to 100% ethyl acetate to obtain 0.40 g of the title compound as a colorless oil; IR (neat) 3031, 2922, 2867, 2126, 1608 cm$^{-1}$; $^1$H NMR (DMSO-d$_6$, 360 MHz) δ3.65–3.75 (m, 2H), 4.16 (q, J=5 Hz, 1H), 4.22 (d, J=11.8 Hz), 4.42 (t, J=5.5 Hz, 1H), 4.47 (d, J=11.8 Hz, 1H), 4.51 (s, 2H), 4.58 (t, J=5.5 Hz, 1H), 4.62 (d, J=12.0 Hz, 1H), 4.68 (d, J=12.0 Hz, 1H), 6.41 (d, J=5.5 Hz, 1H), 6.9–6.95 (m, 2H) 7.1–7.2 (m, 3H), 7.25–7.4 (m, 10H), 8.48 (s, 1H); UV (MeOH) λ$_{max}$, 286 nm; MS (EI+, m/z) 582 (M+H)+.

EXAMPLE 4

Synthesis of 9-β-D-Arabinofuranosyl-2-fluoroadenine

6-Azido-2-fluoro-9-(2,3,5-tri-O-benzyl-β-D-arabinofuranosyl)purine (0.19 g) was dissolved in 2-methoxyethanol (20 mL) with palladium (II) chloride (PdCl$_2$) (20 mg) and activated carbon and the mixture was hydrogenated at 55 pounds per square inch (psi) in a Parr shaker. The reaction was monitored by thin layer chromatography (TLC) until complete. The mixture was then filtered through celite and the filtrate was concentrated in vacuo. Three times, the residue was dissolved in ethanol and reconcentrated. Then the residue was recrystalized from ethanol/water to obtain 0.063 g of the title compound which was consistent in its structure with an authentic sample by IR and TLC.

EXAMPLE 5

Synthesis of 9-(2,3,5-Tri-O-benzyl-β-D-arabinofuranosyl)-2-fluoroadenine

6-Azido-2-fluoro-9-(2,3,5-tri-O-benzyl-β-D-arabinofuranosyl)purine (0.28 g, 0.48 Mmol) was dissolved in warm 2-propanol (3 mL) and then cooled to about 25° C. To the resulting solution was added sodium borohydride (18 mg, 0.48 Mmol) and the mixture was stirred at room temperature for 10 minutes and then at reflux for 15 minutes. The reaction was complete as determined by TLC so it was cooled to room temperature and diluted with water (10 mL). The resulting precipitate was recovered by filtration to obtain 0.19 g of the title compound; mp 159°–161° C. (from toluene/ethanol). This material was identical by IR and TLC with an authentic sample of the title compound.

EXAMPLE 6

Synthesis of 9-β-D-Arabinofuranosyl-2-fluoroadenine

A solution of 2,3,5-tri-O-benzyl-1-α-D-arabinofuranosylchloride (freshly prepared from 1.9 g of 2,3,5-tri-O-benzyl-1-O-p-nitrobenzoyl-D-arabinofuranose) and 6-azido-2-fluoropurine (0.50 g) in anhydrous acetonitrile (30 mL) was stirred for 1 hour at room temperature and then 3 Å molecular sieve (1.26 g, pellets) was added. The mixture was stirred under an inert atmosphere for 3 days and then filtered. The filtrate was concentrated under reduced pressure and the residue was dissolved in 2-propanol and methanol, and then sodium borohydride (0.13 g) was added. After stirring overnight at room temperature the resulting precipitate was collected by filtration. The precipitate was washed with 2-propanol followed by boiling water and then dried to obtain 0.14 g of the title compound. The organic filtrates were concentrated under reduced pressure and the residue was partitioned between dichloromethane and water. The dichloromethane solution was dried over MgSO4 and then filtered and placed on a silica gel column. Elution with 1% methanol in dichloromethane provided an additional 0.10 g of the title compound. Both samples were identical by IR and TLC to an authentic sample of the title compound.

EXAMPLE 7

Synthesis of 2-Fluoroadenine

Triethylamine (0.40 mL) was added via syringe to a solution of 6-azido-2-fluoropurine (0.256 g) and 1,3-propanedithiol (0.29 mL) in methanol (13.5 mL). After 15 minutes the reaction was complete as judged by TLC and a white precipitate had formed. The precipitate was collected by filtration and washed with two 10 mL portions of methanol and then dried to obtain 0.203 g of 2-fluoroadenine, mp>300° C. This material was identical to an authentic sample by TLC, NMR and IR.

EXAMPLE 8

Synthesis of 2-Fluoroadenine

A sample of 6-azido-2-fluoropurine (0.18 g) was dissolved in warm 2-propanol (3 mL) and then cooled to ambient temperature. Sodium borohydride (38 mg) was added in small portions. The vigorous gas evolution was allowed to subside between additions. After the addition was complete the mixture was stirred at ambient temperature and then was heated at 72° C. for 1.5 h. The mixture was then cooled to ambient temperature and diluted with water (10 mL) and the pH was adjusted to 6-7 with 1N hydrochloric acid (HCl) and saturated K2CO3 and then the mixture was concentrated to dryness under vacuum. The residue was triturated in 20 mL of hot water then allowed to cool to ambient temperature. The precipitate was collected by filtration, washed with water and dried to obtain 0.08 g of the title compound as an off-white solid, mp>300° C. This material was identical to an authentic sample by TLC, and IR.

EXAMPLE 9

Synthesis of 9-(2,3,5-Tri-O-benzyl-β-D-Arabinofuranosyl)-2-fluoroadenine

A mixture of 2-fluoroadenine (0.50 g), 2,3,5-tri-O-benzyl-1-α-D-arabinofuranosyl chloride (freshly prepared from 2.22 g of 2,3,5-Tri-O-benzyl-1-O-p-nitrobenzoyl-D-arabinofuranose) and N,N-diisopropylethylamine (0.56 mL) in anhydrous N,N-dimethylformamide (10 mL) was stirred at ambient temperature for 3 days under a nitrogen atmosphere. The mixture was then concentrated under high vacuum and the residue was partitioned between dichloromethane (200 mL) and water (25 mL). The organic phase was washed sequentially with saturated NaCl (50 mL), 1M H3PO4 (50 mL) and saturated NaCl (25 mL), and was then dried over MgSO4 and decolorizing carbon. The dried solution was filtered and concentrated under vacuum. The residue was purified by silica gel chromatography with 1% methanol in dichloromethane as eluant. The appropriate fractions were combined and recrystalized from ethanol/toluene to obtain 0.39 g of the title compound. This material was identical by IR and TLC with an authentic sample.

This invention has been described in particular reference to certain preferred embodiments thereof, but it will be understood that variations and modifications can be effected within the spirit and scope of the invention.

We claim:

1. A compound 6-azido-2-fluoropurine, with the structure:

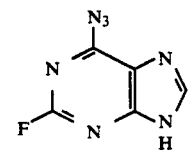

2. A method for preparing 6-azido-2-fluoropurine comprising the following steps:
   (a) reacting 2-amino-6-chloropurine with an alkali metal azide to yield 2-amino-6-azidopurine; and
   (b) diazotizing and fluorinating 2-amino-6-azidopurine to yield 6-azido-2-fluoropurine.

3. A method for preparing 2-fluoradenine comprising the following steps:
   (a) reacting 2-amino-6-chloropurine with an alkali metal azide to yield 2-amino-6-azidopurine;
   (b) diazotizing and fluorinating 2-amino-6-azidopurine to yield 6-azido-2-fluoropurine; and
   (c) reducing 6-azido-2-fluoropurine to yield 2-fluoroadenine.

4. The method of claim 3 wherein step (c) comprises reaction with a dithiol-amine mixture.

5. The method of claim 3 wherein step (c) comprises reaction with a hydride reducing agent.

6. A method according to claim 2, wherein step (a) is conducted in a polar solvent.

7. A method according to claim 2, wherein said alkali metal azide is LiN3, NaN3 or KN3.

8. A method according to claim 2, wherein step (a) is conducted in aqueous dimethylsulfoxide and said alkali metal azide is NaN3.

9. A method according to claim 2, wherein the reaction temperature of step (a) is 50°-130° C.

10. A method according to claim 2, wherein said diazotization agent is an alkyl nitrite or an alkali metal nitrite and said fluorinating agent is HF or HBF4.

11. A method according to claim 2, wherein step (b) is conducted with an anhydrous or aqueous solvent selected from the group consisting of water, pyridine and tetrahydrofuran.

12. A method according to claim 2, wherein the reaction temperature of step (b) is −30°–60° C.

13. A method according to claim 2, wherein step (b) is conducted using an alkyl nitrite, aqueous fluoboric acid and tetrahydrofuran.

14. A method according to claim 8, wherein step (b) is conducted using an alkyl nitrite, aqueous fluoboric acid and tetrahydrofuran.

15. A method according to claim 4, wherein said dithiolamine mixture is a mixture of 1,3-propanediol and triethylamine.

16. A method according to claim 5, wherein said hydride-reducing agent is sodium borohydride.

* * * * *